United States Patent [19]

Koizumi et al.

[11] 4,432,643

[45] Feb. 21, 1984

[54] APPARATUS FOR ATOMIZING A SAMPLE INCLUDING A SLIDABLE PRESSURE MAINTAINING ARRANGEMENT

[75] Inventors: Hideaki Koizumi; Yosio Taiti; Kazuo Moriya; Katsuhito Harada; Kazuo Sato, all of Katsuta, Japan

[73] Assignee: Hitachi, Ltd., Tokyo, Japan

[21] Appl. No.: 245,162

[22] Filed: Mar. 18, 1981

[30] Foreign Application Priority Data

Mar. 19, 1980 [JP] Japan ................................. 55-35557

[51] Int. Cl.³ ........................................... G01N 21/31
[52] U.S. Cl. ..................................................... 356/312
[58] Field of Search ........................................ 356/312

[56] References Cited

U.S. PATENT DOCUMENTS

| | | |
|---|---|---|
| 3,982,834 | 9/1976 | Tamm .................................. 356/312 |
| 4,022,530 | 5/1977 | Braun et al. .......................... 356/312 |
| 4,175,863 | 11/1979 | Tamm et al. ........................ 356/312 |
| 4,202,628 | 5/1980 | Koizumi et al. ..................... 356/312 |

OTHER PUBLICATIONS

"Atomic Absorption HGA-500 Graphite Furnace", Perkin—Elmer Corp., Aug. 1978, p. 4.

Primary Examiner—Vincent P. McGraw
Attorney, Agent, or Firm—Antonelli, Terry & Wands

[57] ABSTRACT

An apparatus for atomizing a sample comprises a cuvette of heating material into which a sample is introduced, a pair of electrodes of supplying an electric current to the cuvette, thereby heating and atomizing the sample, supports of supporting the pair of the electrodes, a means for supplying light to the atomized sample and a means of slidably maintaining at least one of the pair of the electrodes against the cuvette in a predetermined range of contact pressures, where the heating temperature of the cuvette can be maintained constant with improved reproducibility of analytical values.

8 Claims, 5 Drawing Figures

APPARATUS FOR ATOMIZING A SAMPLE INCLUDING A SLIDABLE PRESSURE MAINTAINING ARRANGEMENT

BACKGROUNDS OF THE INVENTION

The present invention relates to the an apparatus for atomizing a sample for flameless atomic absorption analysis, atomic fluorescence analysis and Zeeman atomic absorption analysis (the apparatus will be hereinafter referred to as "atomizer"), and more particularly to an atomizer, using a cuvette made of carbon, such as graphite, tungsten, tantalum, etc. as a heating material.

A graphite atomizer using a graphite tubular cuvette will be explained below as a typical atomizer.

The graphite atomizer is to perform atomic absorption analysis by supplying a large amount of electric current to a graphite tubular cuvette from a pair of electrodes connected to the cuvette, thereby heating the cuvette and a sample introduced into the cuvette, and decomposing and atomizing the sample, and passing a light from a source of atomic spectra through the atomized vapor formed in the cuvette.

When polar pieces (magnet) are provided at both sides of the graphite tubular cuvette to apply a magnetic field to the atomized sample, the absorption spectral lines are split owing to Zeeman effect. This provides a basic structure of Zeeman atomic absorption analysis utilizing the Zeeman effect, and the Zeeman atomic absorption spectrophotometer based thereon is disclosed in detail in U.S. Pat. No. 4,202,628, and its basic structure and the principle of measurement according to it will be explained below, referring to FIGS. 1 and 2.

In FIG. 1, a light source 1 emits light with a single wavelength including two polarizing components $P_V$ and $P_M$ perpendicular to each other. A detector 2 is disposed on the optical path of the light source to receive the light. An atomizer 3 including a graphite tubular cuvette is disposed on the optical path between the light source 1 and the detector 2, and polar pieces 4 and 4' are provided at both sides of the cuvette to produce a magnetic field. A spectrometer 5 is disposed on the optical path between the atomizer 3 and the detector 2 to spectroscopically analyze the light from the atomizer 3. A polarization discriminator 6 is disposed on the optical path between the spectrometer 5 and the detector 2, and discriminates the two orthogonal polarizing components $P_V$ and $P_H$ from the light source 1.

The light having the two polarizing components $P_V$ and $P_H$ perpendicular to each other passes through the atomized sample in the atomizer 3 to produce absorption spectral lines, which are divided into three components as shown in FIG. 2 by the magnetic field H of polar pieces 4 and 4'. The three components are the first absorption spectral line component 21 having substantially a wavelength $\lambda_R$ of light 20 emitted from the light source 1, and the second and third absorption spectral line components 22 and 23 of wave length $\lambda_R + \Delta\lambda$ and $\lambda_R - \Delta\lambda$, respectively, spaced apart by $\pm\Delta\lambda$ from the wavelength $\lambda_R$ of the first absorption spectral line component 21. The first absorption component 21 is characteristically absorbed only by the polarizing component with an oscillation surface 24 parallel to the magnetic field H, and the second and third absorption components 22 and 23 are, on the other hand, characteristically absorbed only by the polarizing component with oscillation surfaces 25 and 26 perpendicular to the magnetic field H. The light from the light source 1 includes the polarizing component $P_V$ with an oscillation surface orthogonal to the magnetic field H, and the polarizing component $P_H$ having an oscillating surface parallel to the magnetic field H. Thus, only the component $P_H$ is absorbed by the first absorption component 21, and the component $P_V$ is not absorbed by the first absorption component 21 or by the second and third absorption components 22 and 23, because the component $P_H$ coincides with the first absorption component 21 in absorption wavelength position and absorption oscillation surface, while the component $P_V$ coincides with the first absorption component 21 in absorption wavelength position, and not in the absorption oscillation surface, and further coincides with the second and third lines 22 and 23 in absorption oscillation surface and not in the absorption wavelength position. That is, the component $P_V$ is not absorbed in any case. The component $P_H$, as absorbed by the first absorption component 21 and the component $P_V$, as not absorbed by any of the three absorption components are introduced into the spectrometer 5. The two components $P_V$ and $P_H$ selected in the spectrometer 5 are discriminated in the polarization discriminator 6 simultaneously or in a time-sharing manner. The two polarizing components are emitted into two directions from the discriminator 6 and led to detectors 2 and 2', respectively. A signal difference is measured from the two polarizing components in the detectors 2 and 2' to provide only the atomic absorption without any influence of background absorption.

The cuvette employed in such an analyzer is disclosed in U.S. Pat. Nos. 4,202,628 and 4,022,530.

The U.S. Pat. No. 4,202,628 discloses prevention of condensation or recombination of atomized sample on the cuvette wall by using a cuvette of special form, and the U.S. Pat. No. 4,022,530 discloses supporting of a tubular cuvette under pressure by means of spring washers.

SUMMARY OF THE INVENTION

An object of the present invention is to provide an atomizer in a simple structure for atomic absorption analysis and atomic fluorescence analysis, particularly for Zeeman atomic absorption analysis, under uniform contact pressure applied to a cuvette with an improved reproducibility of analytical value.

The present invention provides an apparatus for atomizing a sample, which comprises a cuvette of heating material into which a sample is introduced, a pair of electrodes for supplying an electric current to the cuvette, thereby heating the cuvette and the sample, and atomizing the sample, supports for supporting the pair of the electrodes, a means of supplying light to the atomized sample, and a means for slidably maintaining at least one of the pair of the electrodes against the cuvette in a predetermined range of contact pressure.

The present inventors have studied a cause of poor reproducibility in the conventional atomizer using particularly a graphite tubular cuvette, which will be hereinafter referred to as "graphite atomizer", and have found the following facts. That is, by measuring resistances at the respective parts of graphite atomizer, results of Table 1 have been obtained.

TABLE 1

| Parts of graphite atomizer | Resistance (mΩ) |
| --- | --- |
| Graphite tubular cuvette | 9.58–11.72 |

TABLE 1-continued

| Parts of graphite atomizer | Resistance (mΩ) |
|---|---|
| Contact between graphite tubular cuvette and graphite electrode | 4.88–5.90 (×2)* |
| Contact between graphite electrode and metallic electrode | 0.17–0.22 (×2)* |
| Contact between metallic electrode and electrode support | 0.03–0.10 (×2)* |

Remarks:
*means two locations of contact.

As is evident from Table 1, the main resistance in the circuit resides in the contact between the graphite tubular cuvette and the graphite electrode, besides the graphite tubular cuvette. To reduce the contact resistance between the graphite tubular cuvette and the graphite electrode, the graphite tubular cuvette and the graphite electrode must be fabricated in one body, but the graphite tubular cuvette must be exchanged with a fresh one frequently, for example, after the atomization analysis of 50–100 samples at the maximum temperature, due to the deterioration of the cuvette, and thus the integrated fabrication of the graphite tubular cuvette and the graphite electrode is commercially not preferable. Thus, the graphite tubular cuvette has been so far in such a structure as to hold it between a pair of graphite electrodes.

The present inventors have further studied correlations between contact pressures applied to the graphite tubular cuvette and contact resistances between the graphite tubular cuvette and the graphite electrode, and have obtained the results as shown in FIG. 3. It is seen from FIG. 3 that the contact resistance greatly depends upon the contact pressure. Under a lower contact pressure, the contact resistance will be larger than the resistance of the graphite tubular cuvette itself. In the case of stable heat generation with constant current electrodes, the amount of heat generated Q will be given by:

$$Q = I^2(R_T + R_C)$$

where $R_T$ represents the resistance of the graphite tubular cuvette itself, $R_C$ the contact resistance and I a current flowing through the circuit.

Temperature at the inside of graphite tubular cuvette depends upon the amount of heat generated Q. As is obvious from FIG. 3, the contact resistance $R_C$ greatly changes even with a small change in the contact pressure in the range of lower contact pressure, and, thus, the heating temperature of the cuvette is considerably changed due to the change in the amount of heat generated Q. That is, the density of atomized vapor changes correspondingly. In other words, analytical values cannot be obtained with good reproducibility.

Thus, it is necessary to apply the contact pressure in a specific range permitting little change in contact resistance. That is, it is seen from FIG. 3 that a change in the contact resistance is about 5 mΩ with a change in contact pressure from 3 to 4 kg/cm², whereas the change in contact resistance is only 0.5 mΩ with a change in contact pressure from 15 to 16 kg/cm², and thus the change in contact resistance can be reduced to one-tenth. The present inventors have found that the contact pressure must be at least about 8 kg/cm² to suppress the change in contact resistance. Thus, the contact between the graphite tubular cuvette and the graphite electrode must be kept always under a contact pressure of at least about 8 kg/cm². The graphite tubular cuvette, however, expands with increasing heating temperature and contracts with decreasing heating temperature. According to calculation and actual observation, a graphite tubular cuvette, 40 mm long, expands by 0.5 mm, when heated from room temperature to 3,000° C. If both electrodes holding the graphite tubular cuvette are fixed, a very large force will be caused by expansion at the contacts. The present inventors have found that at least one of a pair of electrodes must be slidable to keep the contact pressure always under a predetermined range, even if the length of the graphite tubular cuvette is changed by expansion.

The present inventors have further found that an atomizer must be in a structure capable of adjusting the contact pressure by use of two slide shafts parallel to each other, each slide shaft having at least one slide bearing so as to make at least one of the graphite electrodes uniformly and smoothly slidable while applying the contact pressure to the graphite tubular cuvette in a predetermined range.

The present invention will be described in detail, referring to the accompanying drawings.

PREFERRED EMBODIMENTS OF THE INVENTION

Figure 4:
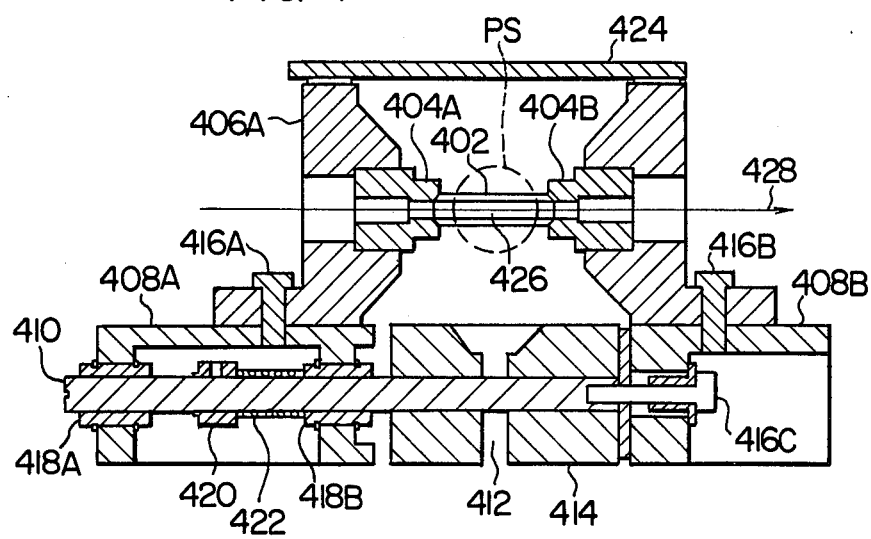
FIG. 4 is a cross-sectional front view of one embodiment of a graphite atomizer according to the present invention for a system for Zeeman atomic absorption analysis.
Figure 5:
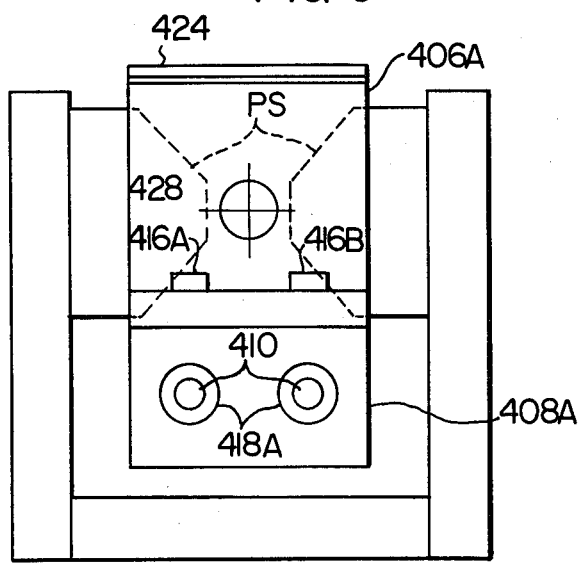
FIG. 5 is a left side view of the atomizer of FIG. 4.

In FIGS. 4 and 5, a graphite tubular cuvette 402 is supported by a pair of graphite electrodes 404A and 404B provided at both ends of the cuvette 402, and the graphite electrodes 404A and 404B are engaged with metallic electrodes 406A and 406B, respectively, and supported thereby. The metallic electrodes 406A and 406B are fixed to electrode supports 408A and 408B, respectively, by bolts 416A and 416B. The electrode supports 408A and 408B are connected to each other through two parallel slide shafts 410. A member 414 having a purge gas inlet 412 is provided between the electrode supports 408A and 408B. The slide shafts 410 are fixed to the electrode support 408B at one end by means of bolts 416C, and there are slide bearings 418A and 418B between the slide shafts 410 and the electrode support 408A. Thus, the graphite electrode 404A, the metallic electrode 406A and the electrode support 408A are slidable on and along the slide shafts 410. Stoppers 420 are fixed each to the slide shafts 410, and there are springs 422 between the stoppers 420 and the slide bearings 418B to apply a pressure to the electrode support 408A, the metallic electrode 406A and the graphite electrode 404A always toward the right side on FIG. 4 through the slide bearings 418B. Thus, the contact pressure is always applied to between the cuvette 402 and the graphite electrodes 404A and 404B by the springs 422. The pressure can be adjusted by adjusting the position of the stoppers 420 toward the right side or the left side on FIG. 4. Numeral 424 is a cover provided between the metallic electrodes 406A and 406B.

When a sample 426 is introduced into the cuvette 402 and an electric current of maximum 400A is supplied to the cuvette from a power cable (not shown in the drawing) connected to the electrode supports 408A and 408B, the cuvette 402 is heated, and the sample in the cuvette is decomposed and atomized. Then, light 428 from a light source (not shown in the drawing) is passed along the center line of the cuvette 402 and through the atomized vapor in the cuvette 402 to conduct atomic absorption analysis.

The cuvette 402 expands in the axial direction by the heating, but the electrode support 408A is slidably supported on the slide shafts 410 through the slide bearings 418A and 418B, and thus the graphite electrode 404A, the metallic electrode 406A and the electrode support 408A slide on and along the slide shafts 410 toward the left side on FIG. 4 against the force of springs 422. Thus, the contact pressure between the cuvette 402 and the graphite electrode 404A and 404B can be kept in a predetermined range, though changed a little, and accurate control heating temperature of cuvette 402 can be thus made with good reproducibility of analytical value.

In the foregoing embodiment, the slide shafts 410 are provided between the electrode supports 408A and 408B, but they can be provided between the metallic electrodes 406A and 406B.

In FIGS. 4 and 5, pole pieces PS (magnet) essential for the atomic absorption analysis based on Zeeman effect, are provided at both sides of the cuvette 402 between the graphite electrodes 404A and 404B.

In the foregoing embodiment, the slide shafts 410 are fixed at one end and slidable at another, but they may be slidable at both ends.

Figure 1:
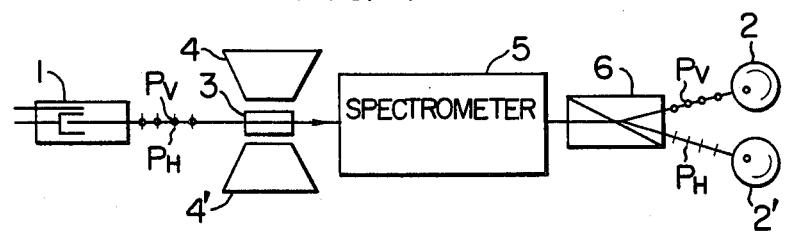
FIG. 1 is a schematic flow diagram of a system for Zeeman atomic absorption analysis to which the present atomizer is applied.
Figure 2:
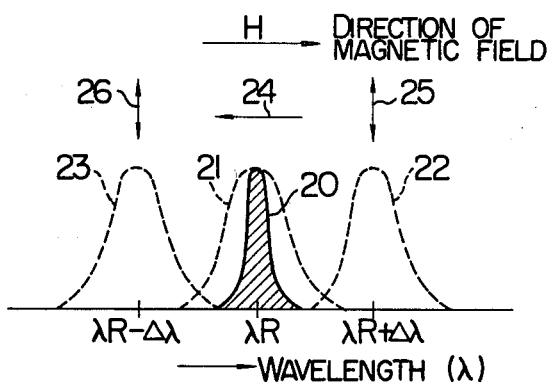
FIG. 2 shows an example of the principle of measurement according to the system of FIG. 1.
Figure 3:
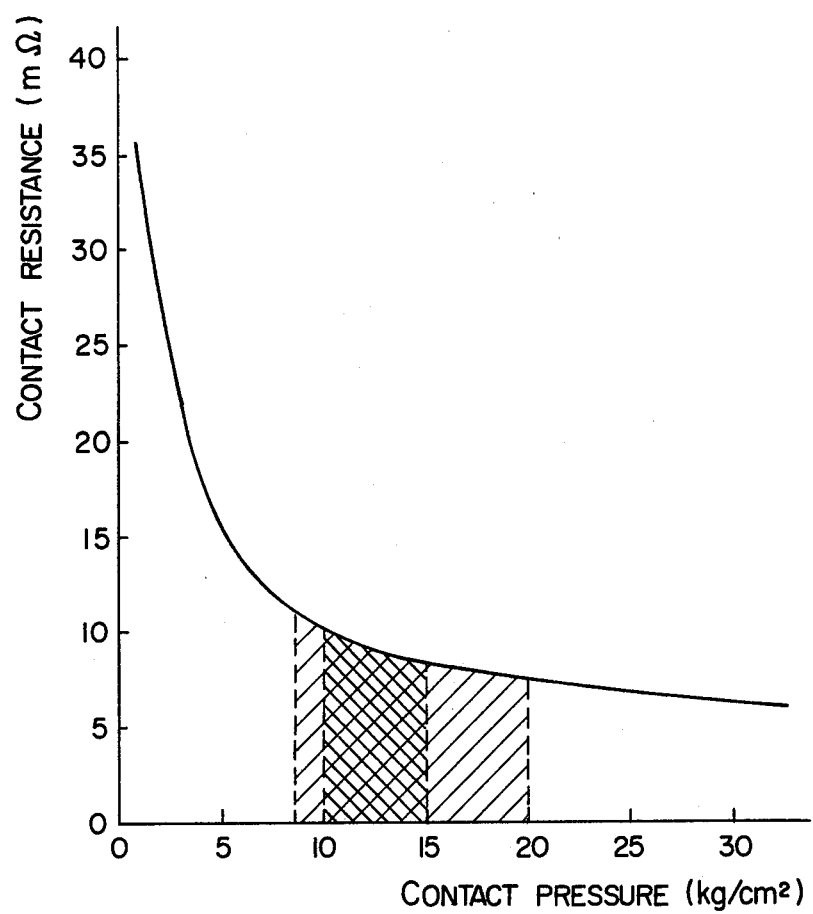
FIG. 3 is a diagram showing correlations between the contact resistance between a graphite tubular cuvette and a graphite electrode and the contact pressure.

It is seen from FIG. 3 that a change in contact resistance will be smaller with increasing contact pressure between the cuvette and the graphite electrode, but when the contact pressure exceeds 20 kg/cm$^2$, the cuvette will be deformed at an elevated temperature. Thus, the contact pressure must be applied thereto in a predetermined range, i.e. a range of 8 to 20 kg/cm$^2$, as in a hatched range in FIG. 3, preferably 10 to 15 kg/cm$^2$, as in a crossed range in FIG. 3.

When another graphite tubular cuvette with different dimension is used and the contact area is changed, the contact pressure will be changed. In that case, the position of the stoppers 420 must be adjusted to adjust the contact pressure to within the predetermined range.

The foregoing embodiment is an example where the present atomizer is applied to the system for Zeeman atomic absorption analysis, but the present atomizer can be used also in other systems for atomic absorption analysis and fluorescence analysis.

According to the present invention, the graphite electrodes supporting the cuvette are slidable in accordance with expansion or contraction of the cuvette, while keeping the contact pressure between the cuvette and the graphite electrodes always in the predetermined range, and consequently the heating temperature of the cuvette can be kept constant. When the contact area of the cuvette is changed by use of another cuvette, the contact pressure can be adjusted to the predetermined range simply by adjusting the position of stoppers to keep the spring force in the predetermined range. Exchange of a deteriorated graphite tubular cuvette with a fresh one can be readily carried out simply by sliding the electrode support along the slide shafts and disengaging the deteriorated one. The contact pressure can be applied evenly to the cuvette by use of two slide shafts parallel to each other, each slide shaft having at least one slide bearing. The atomic absorption analysis can be carried with good reproducibility in the present invention.

The cuvette can be kept under the contact pressure in the predetermined range, and thus can be prevented from deformation or breakage. That is, the life of the cuvette can be prolonged, and more than 200 samples can be analyzed without exchange of the cuvette.

What is claimed is:

1. An apparatus for atomizing a sample, which comprises a cuvette of heating material into which a sample is introduced, a pair of electrodes for supplying an electric current to the cuvette, thereby heating the cuvette and the sample, and atomizing the sample, supports for supporting the pair of electrodes, a means for supplying light to the atomized sample, and a means for slidably maintaining at least one of the pairs of electrodes against the cuvette with a predetermined range of contact pressure during operation of the apparatus, the means for slidably maintaining at least one of the pair of electrodes against the cuvette in a predetermined range of contact pressure comprising two slide shafts arranged in parallel to each other, each slide shaft having at least one slide bearing, at least one spring stopper being fixed on the slide shaft for pressing at least one of the electrodes against the cuvette, and a spring provided between the slide bearing and the spring stopper.

2. An apparatus for atomizing a sample, which comprises a cuvette of heating material into which a sample is introduced, a pair of electrodes for supplying an electric current to the cuvette, thereby heating the cuvette and the sample, and atomizing the sample, supports for supporting the pair of electrodes, a means for supplying light to the atomized sample, and a means for slidably maintaining at least one of the pair of electrodes against the cuvette with a predetermined range of contact pressure during operation of the apparatus, the means for slidbly maintaining at least one of the pair of electrodes against the cuvette in a predetermined range of contact pressure enabling the suppression of changes in contact resistance between the cuvette and the electrodes during operation of the apparatus and including spring means for maintaining the predetermined range of contact pressure in response to expansion and contraction of the cuvette, the predetermined range of contact pressure being 8 to 20 kg/cm$^2$, the means for slidably maintaining at least one of the pair of electrodes against the cuvette in a predetermined range of contact pressure including two slide shafts arranged in parallel to each other, each slide shaft having at least one slide bearing, at least one spring stopper being fixed on the slide shaft for pressing at least one of the electrodes against the cuvette, and the spring means including a spring provided between the slide bearing and the spring stopper.

3. An apparatus according to claim 2, wherein the predetermined range of contact pressure is 10 to 15 kg/cm$^2$.

4. An apparatus according to claim 2, wherein the spring is a spiral spring surrounding the slide shaft.

5. An apparatus for atomizing a sample, which comprises a cuvette of heating material into which a sample is introduced, a pair of electrodes for supplying an electric current to the cuvette, thereby heating the cuvette and the sample, and atomizing the sample, supports for supporting the pair of electrodes, a means for supplying light to the atomized sample, and a means for slidably maintaining at least one of the pairs of electrodes against the cuvette with a predetermined range of contact pressure during operation of the apparatus, the means for slidably maintaining at least one of the pair of electrodes against the cuvette in a predetermined range of contact pressure enabling the suppression of changes in contact resistance between the cuvette and the electrodes during operation of the apparatus and including spring means for maintaining the predetermined range of contact pressure in response to expansion and contraction of the cuvette, the predetermined range of contact pressure being 8 to 20 $kg/cm^2$, the means for slidably maintaining at least one of the pair of electrodes against the cuvette in a predetermined range of contact pressure including at least one slide shaft, and the spring means including a sprial spring surrounding the slide shaft.

6. An apparatus according to claim 5, wherein a pair of pole pieces are arranged at both sides of the electrodes.

7. An apparatus according to claim 5, wherein the cuvette is a graphite tubular cuvette.

8. An apparatus according to claim 5, wherein the predetermined range of contact pressure is 10 to 15 $kg/cm^2$.

* * * * *